United States Patent
Tseng et al.

(10) Patent No.: US 10,225,442 B2
(45) Date of Patent: Mar. 5, 2019

(54) ELECTRONIC DEVICE AND METHOD FOR SENSING AIR QUALITY

(71) Applicant: MediaTek Inc., Hsin-Chu (TW)

(72) Inventors: Kui-Chang Tseng, Kaohsiung (TW); Tsu-Ming Liu, Hsinchu (TW)

(73) Assignee: MEDIATEK INC., Hsin-Chu (TW)

( * ) Notice: Subject to any disclaimer, the term of this patent is extended or adjusted under 35 U.S.C. 154(b) by 367 days.

(21) Appl. No.: 15/000,220

(22) Filed: Jan. 19, 2016

(65) Prior Publication Data

US 2016/0238527 A1    Aug. 18, 2016

Related U.S. Application Data

(60) Provisional application No. 62/116,710, filed on Feb. 16, 2015.

(51) Int. Cl.
*G01N 21/00* (2006.01)
*H04N 5/225* (2006.01)
(Continued)

(52) U.S. Cl.
CPC ....... *H04N 5/2252* (2013.01); *G01N 15/1434* (2013.01); *G01N 21/53* (2013.01);
(Continued)

(58) Field of Classification Search
CPC .... G06F 1/1626; G06F 3/0488; G06F 3/0414; G06F 3/0416; G06F 3/0484; G06F 3/16; G06F 3/016; G06F 1/1686; H04N 7/144; H04N 5/2252; H04N 5/2253; H04N 5/2254; H04N 5/2257; H04N 7/15; H04M 1/0264; G06K 9/00255; G06T 3/60; G01N 15/1434; G01N 21/53; G01N 21/55
(Continued)

(56) References Cited

U.S. PATENT DOCUMENTS 5,428,964 A * 7/1995 Lobdell ................ G05D 27/02
                                                   62/176.6
5,531,801 A * 7/1996 Sewell ................ B01D 47/06
                                                    96/240
(Continued)

FOREIGN PATENT DOCUMENTS

CN    200982953 Y    11/2007
CN    102636621 A    8/2012
(Continued)

Primary Examiner — Georgia Y Epps
Assistant Examiner — Kevin Wyatt
(74) Attorney, Agent, or Firm — McClure, Qualey & Rodack, LLP (57) ABSTRACT

An electronic device for sensing air quality is provided. The electronic device includes a proximity sensor, a processor and a memory. The proximity sensor at least includes a light source and a light sensor. The light source emits light toward particulate matter in air, wherein the light is reflected by a surface of the particulate matter to form reflected light. The light sensor senses the reflected light. The processor is coupled to the proximity sensor, and the memory is operatively coupled to the processor. The processor is configured to execute program code stored in the memory by: obtaining an air quality value corresponding to an intensity value of the reflected light according to an air quality table.

16 Claims, 8 Drawing Sheets

(51) Int. Cl.

| | |
|---|---|
| *H04N 7/14* | (2006.01) |
| *G06F 3/0488* | (2013.01) |
| *G06K 9/00* | (2006.01) |
| *G06T 3/60* | (2006.01) |
| *H04N 7/15* | (2006.01) |
| *G01N 15/14* | (2006.01) |
| *G01N 21/53* | (2006.01) |
| *G01N 21/55* | (2014.01) |
| *G06F 3/041* | (2006.01) |
| *G06F 3/0484* | (2013.01) |
| *G06F 3/16* | (2006.01) |
| *G06F 3/01* | (2006.01) |
| *G06F 1/16* | (2006.01) |
| *H04M 1/02* | (2006.01) |

(52) U.S. Cl.
CPC ........... *G01N 21/55* (2013.01); *G06F 1/1626* (2013.01); *G06F 1/1686* (2013.01); *G06F 3/016* (2013.01); *G06F 3/0414* (2013.01); *G06F 3/0416* (2013.01); *G06F 3/0484* (2013.01); *G06F 3/0488* (2013.01); *G06F 3/16* (2013.01); *G06K 9/00255* (2013.01); *G06T 3/60* (2013.01); *H04M 1/0264* (2013.01); *H04N 5/2253* (2013.01); *H04N 5/2254* (2013.01); *H04N 5/2257* (2013.01); *H04N 7/144* (2013.01); *H04N 7/15* (2013.01); *G01N 2201/062* (2013.01); *G01N 2201/0638* (2013.01); *G06F 2203/04806* (2013.01); *G06F 2203/04808* (2013.01); *H04N 2007/145* (2013.01)

(58) Field of Classification Search
USPC .......................................................... 250/565
See application file for complete search history.

(56) References Cited

U.S. PATENT DOCUMENTS

| | | | | |
|---|---|---|---|---|
| 2008/0265870 | A1* | 10/2008 | Nair | G01N 15/0656 324/105 |
| 2010/0194574 | A1* | 8/2010 | Monk | G01N 21/53 340/627 |
| 2013/0169967 | A1* | 7/2013 | Kanukurthy | A62B 9/006 356/400 |
| 2014/0260692 | A1 | 9/2014 | Sharp | |

FOREIGN PATENT DOCUMENTS

| | | |
|---|---|---|
| CN | 103037050 A | 4/2013 |
| CN | 103353434 A | 10/2013 |
| CN | 103454194 A | 12/2013 |
| CN | 103868835 A | 6/2014 |
| CN | 104198349 A | 12/2014 |
| KR | 20030097437 A | 12/2003 |

* cited by examiner

ELECTRONIC DEVICE AND METHOD FOR SENSING AIR QUALITY

CROSS REFERENCE TO RELATED APPLICATIONS

This application claims priority of U.S. Provisional Patent Application No. 62/116,710, filed on Feb. 16, 2015, the entirety of which is incorporated by reference herein.

BACKGROUND OF THE INVENTION

Field of the Invention

Aspects of the present invention relate generally to an electronic device and a method for sensing air quality and, more particularly, to an electronic device and a method for sensing air quality using a proximity sensor.

Description of the Related Art

Electronic devices such as cellular telephones are sometimes provided with proximity sensors. For example, a cellular telephone may be provided with a proximity sensor that is located near an ear speaker on the front face of the cellular telephone. The front face of the cellular telephone may also contain a touch screen display. The proximity sensor may be used to determine when the cellular telephone is near the head of a user.

Currently, the PM 2.5 particle has become a major problem in air pollution. PM 2.5 refers to particles with a diameter of less than or equal to 2.5 micrometers, which can enter people's lungs. It is therefore desirable to have a device with a convenient air quality sensing function to help users monitor air quality. However, existing air quality detection devices are large and relatively expensive. Furthermore, their operation and maintenance often require specialized operators and involve cumbersome processes.

Therefore, in order to decrease the cost of monitoring air quality and to avoid changing the structure of an existing electronic device (e.g. a cellular telephone), there is a need for an electronic device and a method for sensing air quality using a proximity sensor.

BRIEF SUMMARY OF THE INVENTION

A detailed description is given in the following embodiments with reference to the accompanying drawings.

Electronic devices and methods for sensing air quality are provided.

In a preferred embodiment, the invention is directed to an electronic device for sensing air quality. The electronic device comprises a proximity sensor, a processor and a memory. The proximity sensor at least comprises a light source and a light sensor. The light source emits light toward particulate matter in air, wherein the light is reflected by a surface of the particulate matter to form reflected light. The light sensor senses the reflected light. The processor is coupled to the proximity sensor, and the memory is operatively coupled to the processor. The processor is configured to execute program code stored in the memory by obtaining an air quality value corresponding to an intensity value of the reflected light according to an air quality table.

In some embodiments, the air quality table is used for mapping the intensity values of the reflected light to air quality values; and the processor obtains the air quality value based on the intensity value of the reflected light. In some embodiments, the electronic device further comprises a PM 2.5 filter, wherein the PM 2.5 filter comprises a chamber having at least a size selective inlet, wherein the size selective inlet controls a size of the particulate matter flowing through the chamber, wherein an aerodynamic diameter of the particulate matter is less than 2.5 µm. In some embodiments, before obtaining the air quality value corresponding to the intensity value of the reflected light according to the air quality table, the processor further executes the program code stored in the memory by: determining whether the PM 2.5 filter is installed at the top of the proximity sensor for controlling the size of the particulate matter flowing through the chamber; and obtaining a PM 2.5 quality value corresponding to the intensity value of the reflected light according to a PM 2.5 quality table after the processor determines that the PM 2.5 filter is installed at the top of the proximity sensor for controlling the size of the particulate matter flowing through the chamber. In some embodiments, the PM 2.5 quality table is used for mapping the intensity values of the reflected light to PM 2.5 quality values; and the processor obtains the PM 2.5 quality value based on the intensity value of the reflected light. In some embodiments, the electronic device further comprises a lens, wherein the lens is disposed on an optical path of the light source and focuses the reflected light to increase sensitivity. In some embodiments, before obtaining the air quality value corresponding to the intensity value of the reflected light according to the air quality table, the processor further executes the program code stored in the memory by: increasing exposure time of the light sensor until a predetermined time when the intensity value of the reflected light sensed by the light sensor is less than a light threshold value. In some embodiments, before obtaining the air quality value corresponding to the intensity value of the reflected light according to the air quality table, the processor further executes the program code stored in the memory by: increasing supply current of the light source for increasing the intensity value of the light when the intensity value of the reflected light sensed by the light sensor is less than a light threshold value. In some embodiments, the processor further executes the program code stored in the memory by: connecting to a regulator device; comparing the air quality value to a predetermined threshold; determining whether the air quality value exceeds the predetermined threshold; and transmitting a signal to the regulator device after determining that the air quality value exceeds the predetermined threshold, wherein the signal is used to instruct the regulator device to purify the air.

In a preferred embodiment, the invention is directed to a method for sensing air quality, used in an electronic device, comprising: emitting, by a light source of a proximity sensor of the electronic device, light toward particulate matter in air, wherein the light is reflected by a surface of the particulate matter to form reflected light; sensing, by a light sensor of the proximity sensor, the reflected light; and obtaining, by a processor of the electronic device, an air quality value corresponding to an intensity value of the reflected light according to an air quality table.

In some embodiments, the air quality table is used for mapping the intensity values of the reflected light to air quality values, and the method further comprises: determining, by the processor, the air quality value based on the intensity value of the reflected light. In some embodiments, the method further comprises: controlling, by a size selective inlet of a PM 2.5 filter of the electronic device, a size of the particulate matter flowing through a chamber of the PM 2.5 filter, wherein an aerodynamic diameter of the particulate matter is less than 2.5 µm. In some embodiments, before obtaining the air quality value corresponding to the intensity value of the reflected light according to the air quality table, the method further comprises: determining whether the PM 2.5 filter is installed at the top of the proximity sensor for controlling the size of the particulate matter flowing through the chamber; and obtaining a PM 2.5 quality value corresponding to the intensity value of the reflected light according to a PM 2.5 quality table after the processor determines that the PM 2.5 filter is installed at the top of the proximity sensor for controlling the size of the particulate matter flowing through the chamber. In some embodiments, the PM 2.5 quality table is used for mapping the intensity values of the reflected light to PM 2.5 quality values, and the method further comprises: determining, by the processor, the PM 2.5 quality value based on the intensity value of the reflected light. In some embodiments, the electronic device further comprises a lens disposed on an optical path of the proximity sensor, and the method further comprises: focusing, by the lens, the reflected light to increase sensitivity. In some embodiments, before obtaining the air quality value corresponding to the intensity value of the reflected light according to the air quality table, the method further comprises: increasing, by the processor, exposure time of the light sensor until a predetermined time when the intensity value of the reflected light sensed by the light sensor is less than a light threshold value. In some embodiments, before obtaining the air quality value corresponding to the intensity value of the reflected light according to the air quality table, the method further comprises: increasing, by the processor, supply current of the light source for increasing luminance of the light when the intensity value of the reflected light sensed by the light sensor is less than a light threshold value. In some embodiments, the method further comprises: connecting to a regulator device; comparing the air quality value to a predetermined threshold; determining whether the air quality value exceeds the predetermined threshold; transmitting a signal to the regulator device after determining that the air quality value exceeds the predetermined threshold, wherein the signal is used to instruct the regulator device to purify the air.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Several exemplary embodiments of the present disclosure are described with reference to FIGS. 1 through 8, which generally relate to an electronic device and a method for sensing air quality. It should be understood that the following disclosure provides various embodiments as examples for implementing different features of the present disclosure. Specific examples of components and arrangements are described in the following to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various described embodiments and/or configurations.

Figure 1:
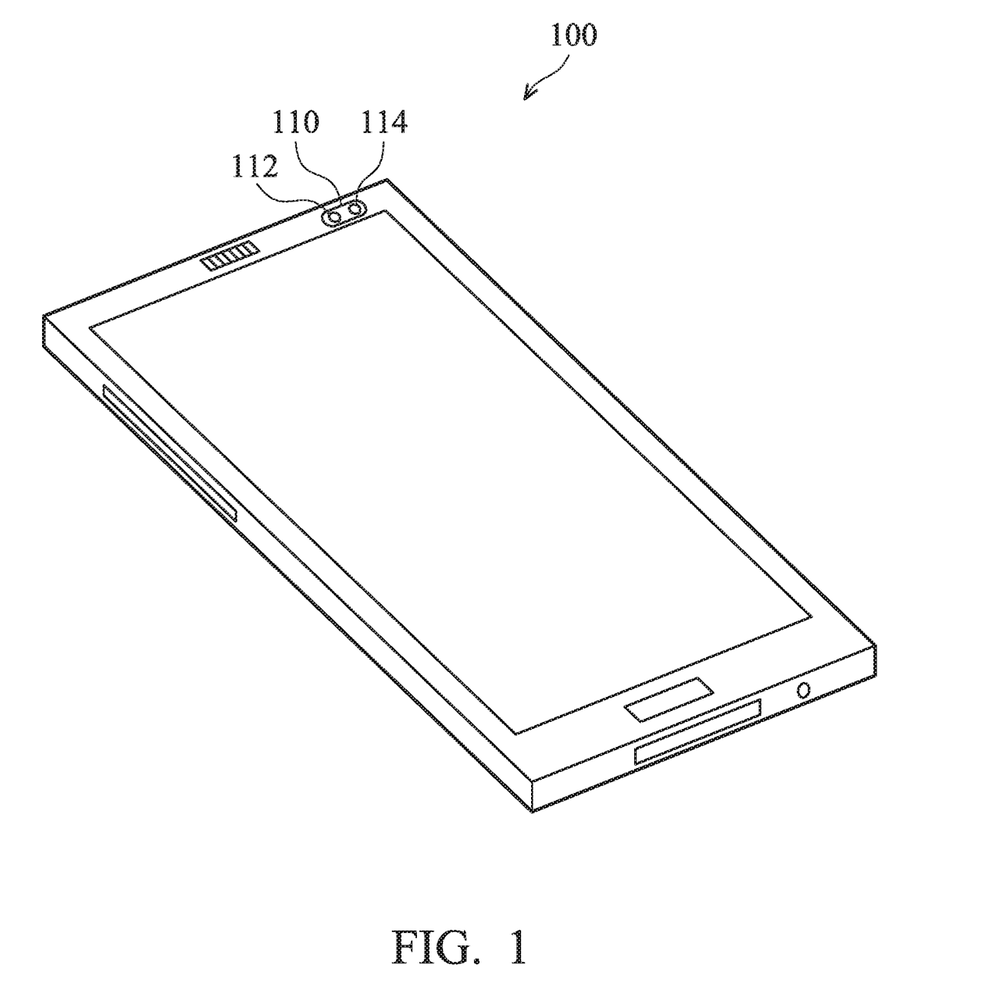
FIG. 1 is a schematic diagram illustrating an electronic device with a proximity sensor according to an embodiment of the present invention.

FIG. 1 is a schematic diagram illustrating an electronic device 100 with a proximity sensor according to an embodiment of the present invention. Electronic devices such as the electronic device 100 of FIG. 1 may be cellular telephones, media players, other handheld portable devices, somewhat smaller portable devices such as wrist-watch devices, or other wearable or miniature devices, or other electronic equipment.

As shown in FIG. 1, a proximity sensor 110 can be installed in the electronic device 100 and co-located in the electronic device 100 (i.e., in-device). The proximity sensor 110 may be a light-based proximity sensor and may include a light source 112 and a light sensor 114. The light source 112 is used to project/emit light toward an object in external air outside the housing of the electronic device 100. The light sensor 114 can sense reflected light in the external air from the light source 112, wherein the reflected light has reflected by a surface of the object in the external air. In one embodiment, the light source 112 may be an infrared light-emitting diode (IR LED) light source, and the light sensor 114 may be a photodetector based on a transistor or a photodiode.

Figure 2:
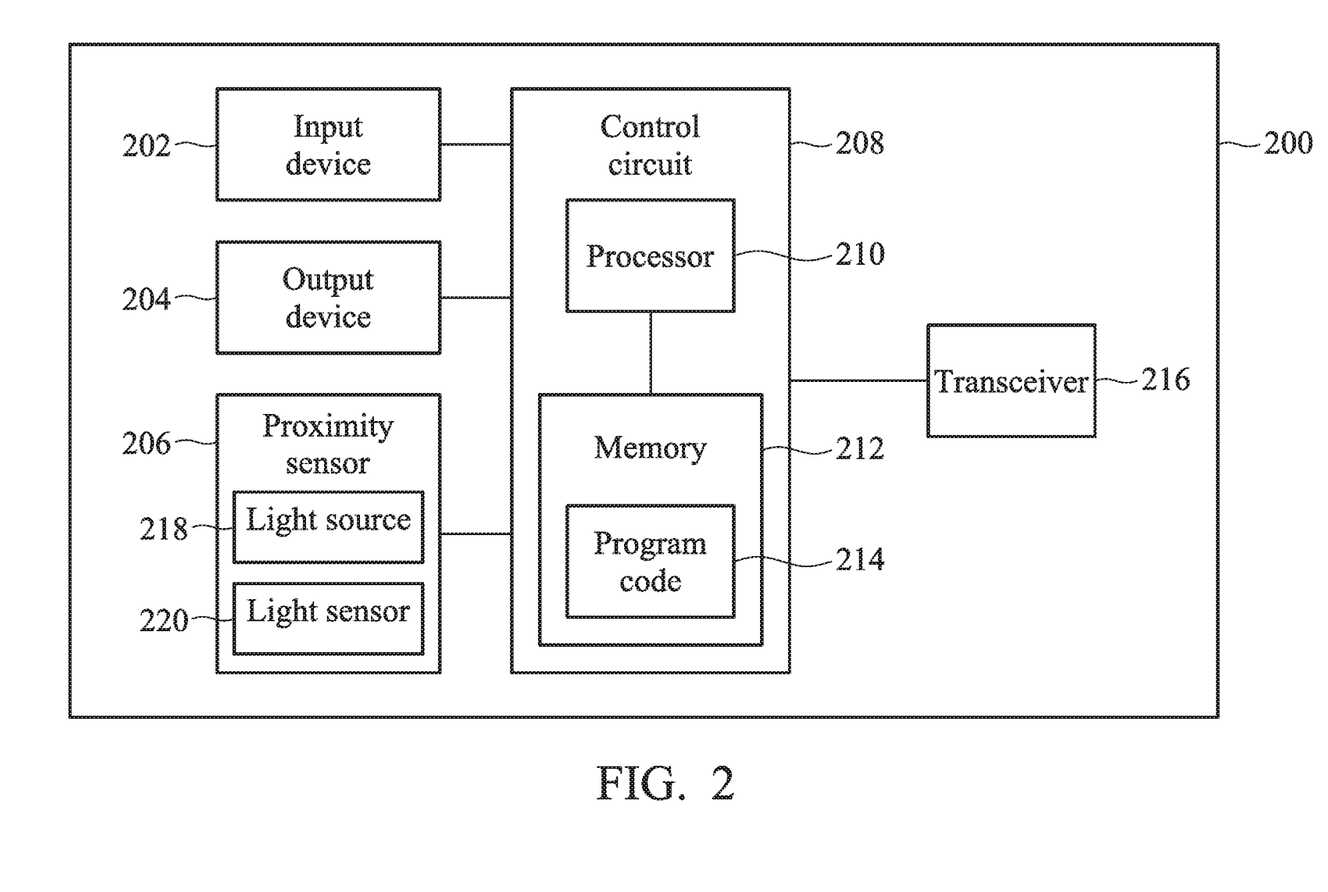
FIG. 2 is a functional block diagram of an electronic device for sensing air quality according to an embodiment of the present invention.

FIG. 2 is a functional block diagram of an electronic device 200 for sensing air quality according to an embodiment of the present invention. As shown in FIG. 2, the electronic device 200 can be utilized for realizing the electronic device 100 in FIG. 1. The electronic device 200 may include an input device 202, an output device 204, a proximity sensor 206, a control circuit 208, a processor 210, a memory 212, program code 214, and a transceiver 216.

The control circuit 208 executes the program code 214 in the memory 212 through the processor 210, thereby controlling the operation of the electronic device 200. The electronic device 200 can receive signals input by a user through the input device 202, such as a keyboard or keypad, and can output images and sounds through the output device 204, such as a monitor or speakers. The proximity sensor 206 can at least comprise a light source 218 and a light sensor 220. Similarly, the proximity sensor 206 can be utilized for realizing the proximity sensor 110 in FIG. 1. The light source 218 and the light sensor 220 can be utilized for realizing the light source 112 and the light sensor 114 in FIG. 1, respectively. The light source 218 can be used to emit light toward particulate matter in the external air, wherein the light is reflected by a surface of the particulate matter in the external air to form reflected light. The light sensor 220 can be used to sense the reflected light in the external air. The transceiver 216 is used to for receiving and transmitting wireless signals, delivering received signals to the control circuit 208 wirelessly, and outputting signals generated by the control circuit 208.

In one embodiment, the processor 210 may obtain an air quality value corresponding to an intensity value of the reflected light according to an air quality table. A detailed description of this process will be described below.

According to one embodiment of the present invention, the memory 212 is database for storing data. In an exemplary embodiment, the memory 212 stores the air quality table used for mapping the intensity values of the reflected light to air quality values, so that the processor can obtain the air quality value based on the intensity value of the reflected light.

Figure 3:
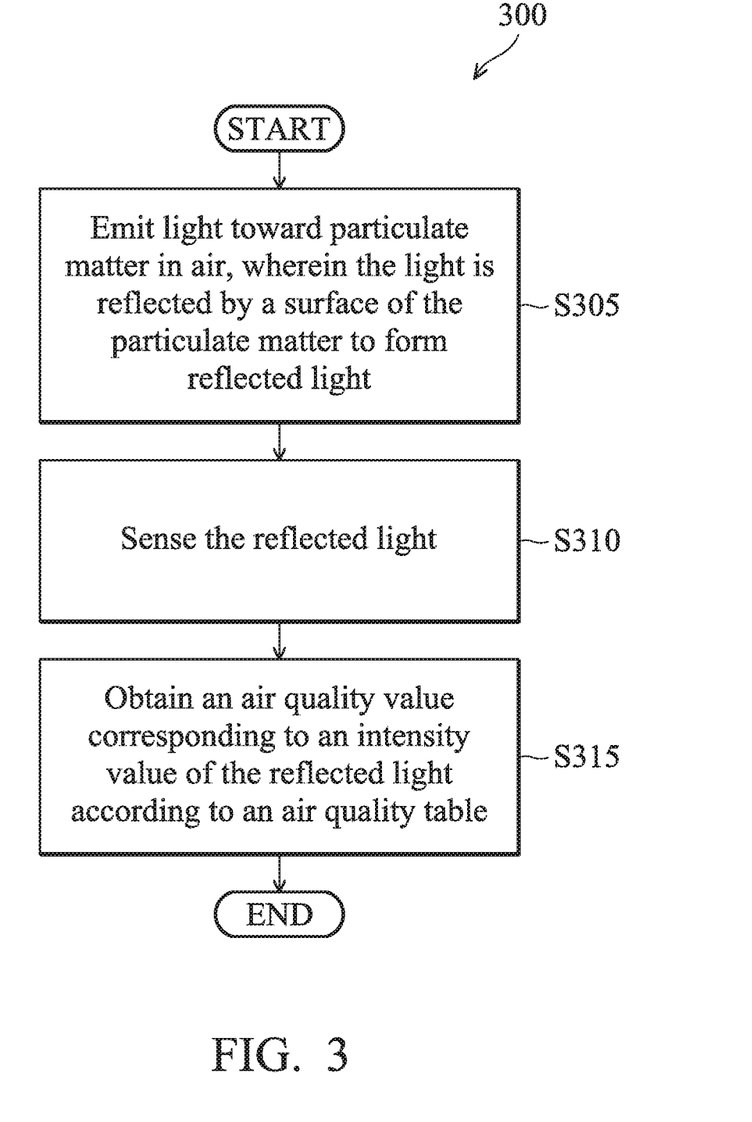
FIG. 3 is a flow diagram illustrating a method for sensing air quality according to an embodiment of the present invention with reference to FIG. 2.

FIG. 3 is a flow diagram illustrating a method 300 for sensing air quality according to an embodiment of the present invention with reference to FIG. 2. It should be noted that the method is performed by the electronic device 200 of FIG. 2. First, in step S305, the light source of a proximity sensor emits light toward particulate matter in air, wherein the light is reflected by a surface of the particulate matter to form reflected light. Next, in step S310, the light sensor of the proximity sensor senses the reflected light. In step S315, the processor of the electronic device obtains an air quality value corresponding to an intensity value of the reflected light according to an air quality table. In the embodiment, the air quality table is used for mapping the intensity values of the reflected light to air quality values, so that the processor can obtain the air quality value based on the intensity value of the reflected light. For instance, the air quality table may be a two-column and multi-row table, wherein for each row of the air quality table contains a number of the intensity value of the reflected light and a corresponding air quality value.

Figure 4:
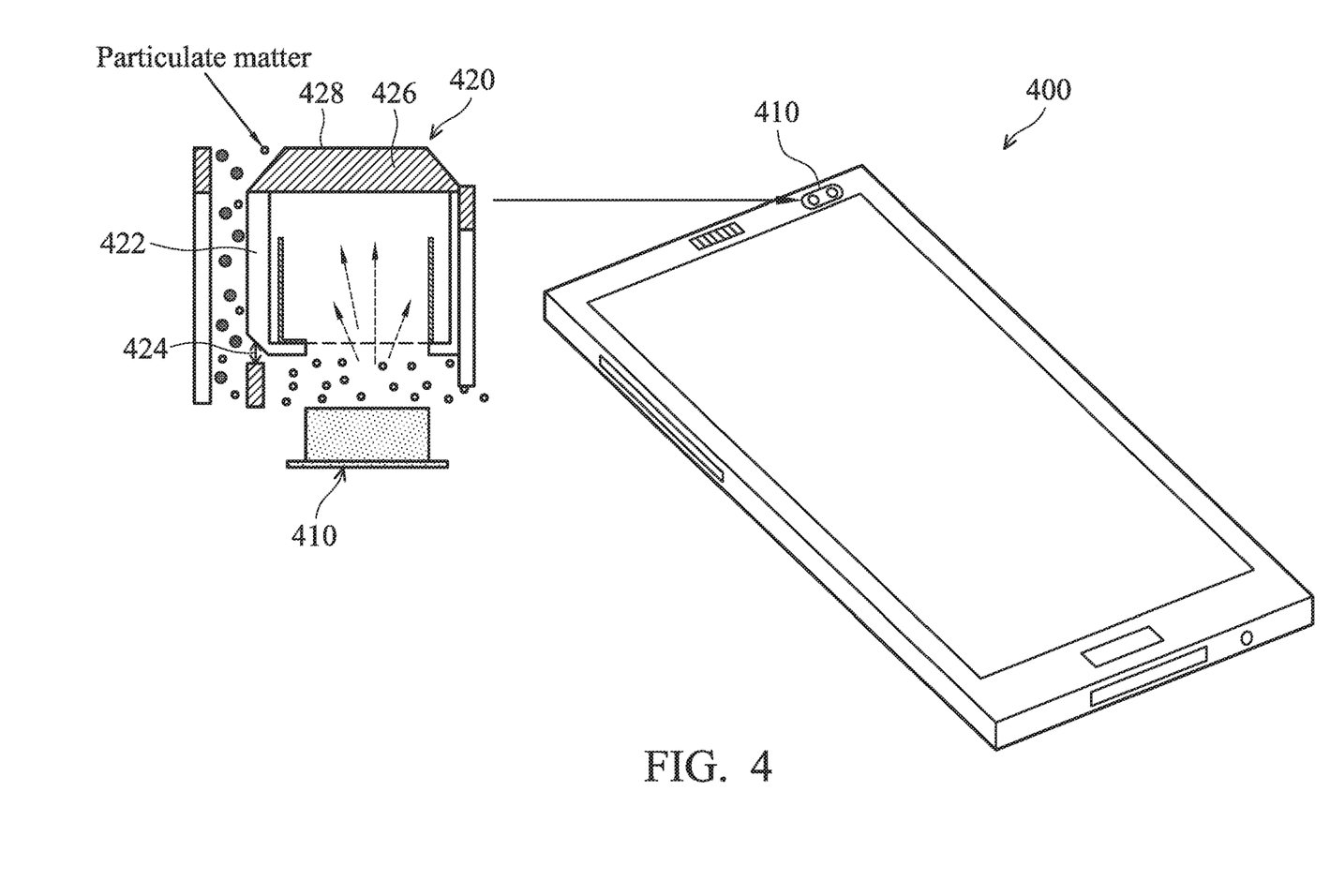
FIG. 4 is a schematic diagram illustrating an electronic device with a PM 2.5 filter according to an embodiment of the present invention.

In another embodiment, the electronic device for sensing air quality may further comprise a PM 2.5 filter. FIG. 4 is a schematic diagram illustrating an electronic device 400 with a PM 2.5 filter 420 according to an embodiment of the present invention. The PM 2.5 filter 420 can be installed at the top of the proximity sensor 410, and at least comprises a chamber 422 having at least a size selective inlet 424, a fan 426 and an opening 428. The size selective inlet 424 is capable of controlling the size of the particulate matter flowing through the chamber 422. The fan 426 is disposed on the top of the chamber 422 and is used to draw the air through the size selective inlet 424 into the chamber 422, and exhausts through the opening 428. In the embodiment, a diameter of the size selective inlet 424 can be about 2.5 μm to block the particulate matter having an aerodynamic diameter that is greater than or equal to 2.5 μm so that the aerodynamic diameter of the particulate matter in the chamber 422 is less than approximately 2.5 μm. The PM 2.5 filter 420 can be directly attached to the surface of the electronic device 400 to be on top of the proximity sensor 410. Though not explicitly drawn, in another embodiment, the PM 2.5 filter 420 may be integrated with the proximity sensor 410 within the electronic device 400 (i.e. within the housing of the electronic device 400).

Figure 5:
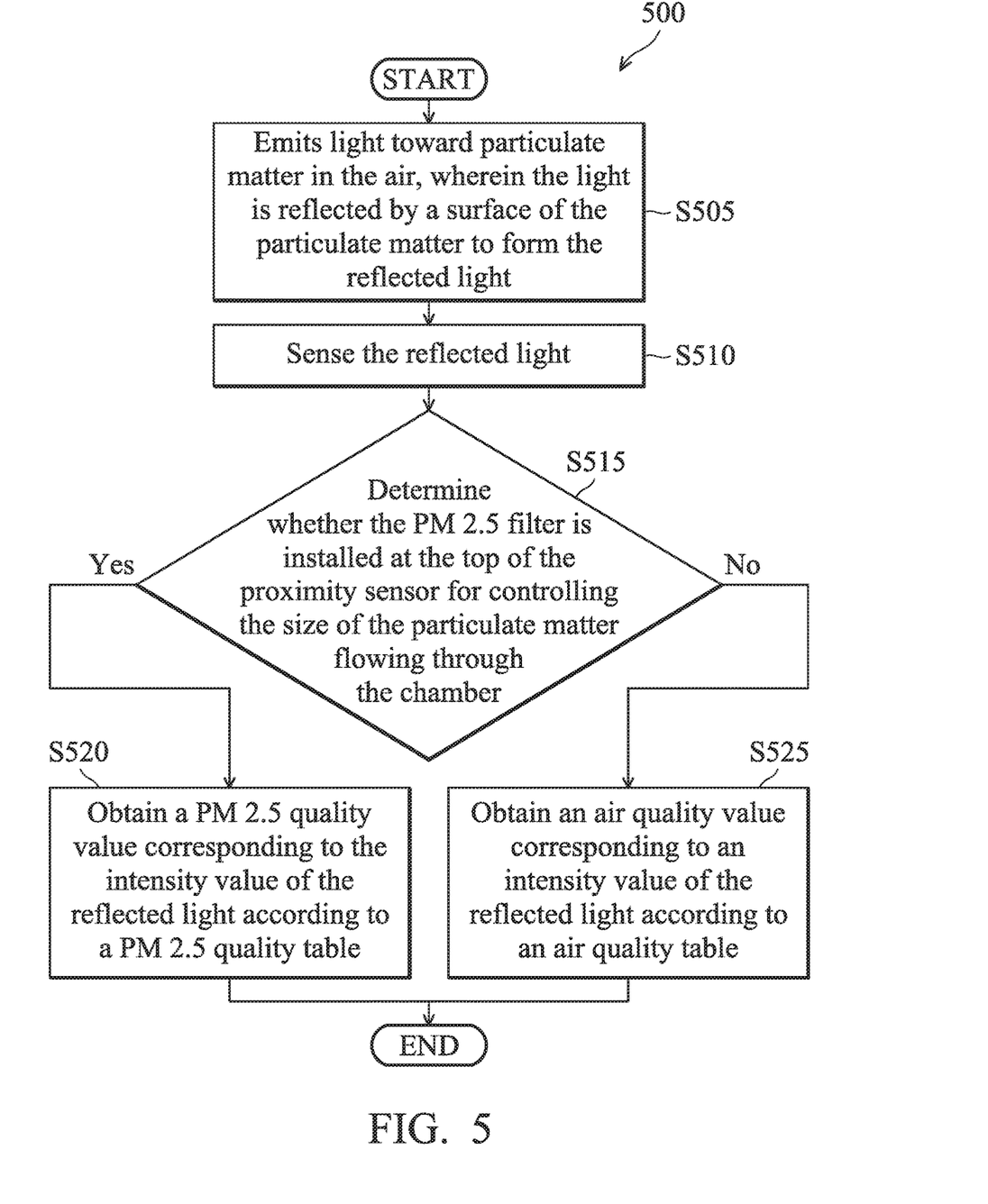
FIG. 5 is a flow diagram illustrating a method for sensing air quality according to an embodiment of the present invention with reference to FIG. 4.

FIG. 5 is a flow diagram illustrating a method 500 for sensing air quality according to an embodiment of the present invention with reference to FIG. 4. It should be noted that the method can be performed by the electronic device 400 of FIG. 4. First, in step S505, the light source of the proximity sensor 410 emits light toward particulate matter in the air, wherein the light is reflected by a surface of the particulate matter to form the reflected light. Next, in step S510, the light sensor of the proximity sensor 410 senses the reflected light. In step S515, the processor of the electronic device 400 determines whether the PM 2.5 filter is installed at the top of the proximity sensor 410 for controlling the size of the particulate matter flowing through the chamber 422. This determination may be carried out by detecting mechanically whether the PM 2.5 filter 420 is integrated with the electronic device 400. Note that when the PM 2.5 filter 420 is installed at the top of the proximity sensor, the aerodynamic diameter of the particulate matter in the chamber 422 is less than 2.5 μm since the particulate matter with a diameter greater than or equal to 2.5 μm is not allowed to enter into the chamber 422. When the PM 2.5 filter 420 is not installed at the top of the proximity sensor 410, the proximity sensor 410 can sense the air quality of the whole particulate matter in the external air rather than only the particulate matter with a diameter less than 2.5 μm. In other words, the particulate matter reflecting the light can be the particulate matter with an aerodynamic diameter that is greater than or equal to 2.5 μm and/or the particulate matter with an aerodynamic diameter that is less than 2.5 μm.

When the processor determines that the PM 2.5 filter 420 is installed at the top of the proximity sensor 410 for controlling the size of the particulate matter flowing through the chamber ("Yes" in step S515), in step S520, the processor obtains a PM 2.5 quality value corresponding to the intensity value of the reflected light according to a PM 2.5 quality table. In the embodiment, the PM 2.5 quality table is used for mapping the intensity values of the reflected light to PM 2.5 quality values so that the processor can obtain the PM 2.5 quality value based on the intensity value of the reflected light. Larger intensity value indicates higher density of the particulate matter with a diameter that is less than 2.5 μm. Note that here the reflected light comes from the particulate matter with a diameter less than 2.5 μm inside the chamber.

Referring back to step S515, when the processor determines that the PM 2.5 420 filter is not installed at the top of the proximity sensor 410 for controlling the size of the particulate matter flowing through the chamber 422 ("No" in step S515), in step S525, the processor obtains an air quality value corresponding to an intensity value of the reflected light according to an air quality table. In the embodiment, the air quality table is used for mapping the intensity values of the reflected light to air quality values, so that the processor can obtain the air quality value based on the intensity value of the reflected light. Note that here the reflected light comes from the particulate matter with a diameter less than 2.5 μm and/or a diameter greater than or equal to 2.5 μm.

It should be noted that before step S520 or step S525, the processor can increase exposure time of the light sensor until a predetermined time when the intensity value of the reflected light sensed by the light sensor is less than a light threshold value. In one embodiment, the light threshold value may be stored at various locations including, but not limited to, the memory included in the electronic device, or a cloud server communicating with the electronic device wirelessly. In other embodiment, before step S520 or step S525, the processor can increase supply current of the light source for increasing the intensity value of the light when the intensity value of the reflected light sensed by the light sensor is less than the light threshold value.

Figure 6:
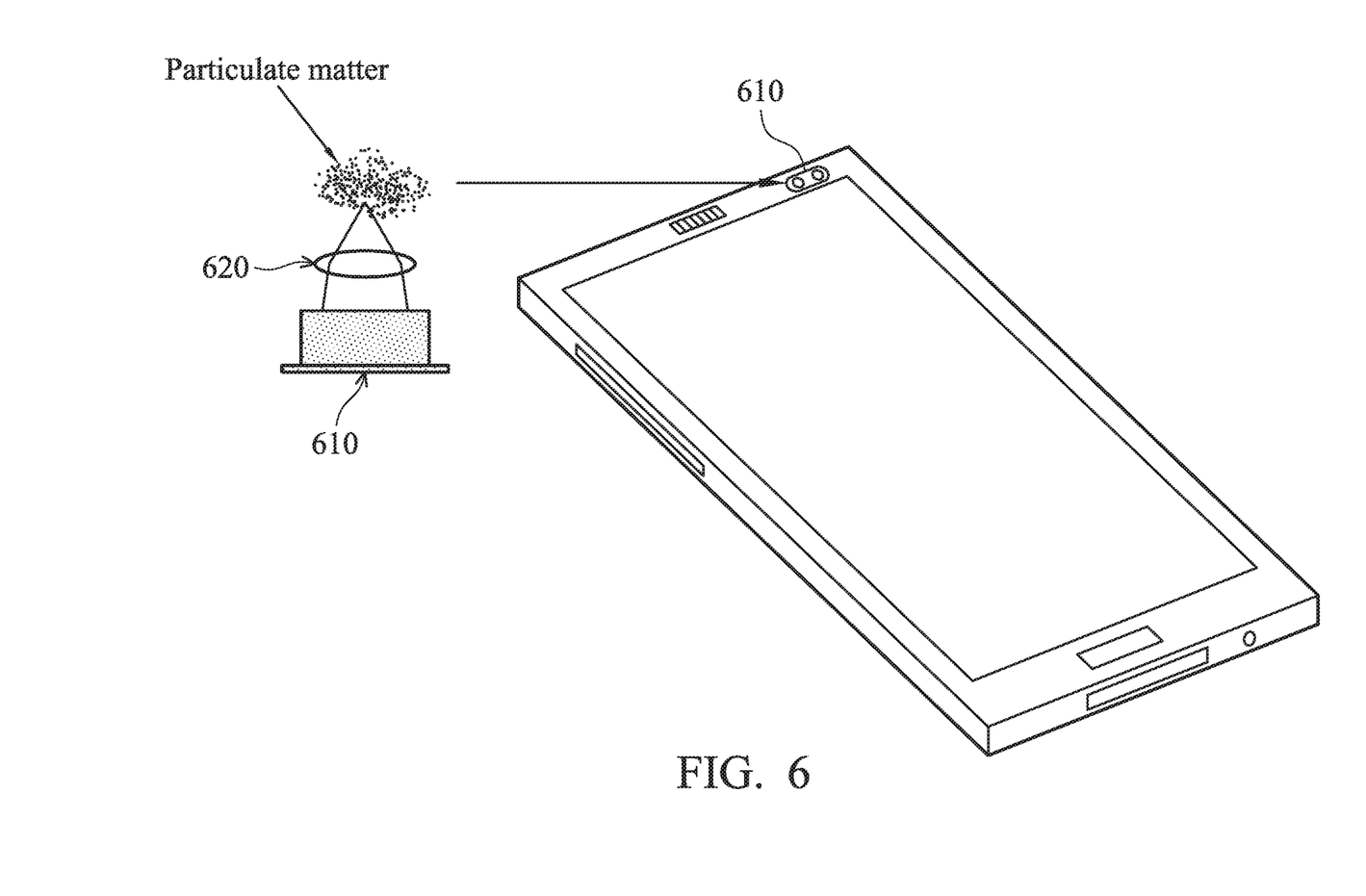
FIG. 6 is a schematic diagram illustrating an electronic device with a lens according to an embodiment of the present invention.

In another embodiment, a lens 620 (instead of a PM 2.5 filter 420 as in FIG. 4) can be disposed on an optical path of the light source and focuses the reflected light to increase sensitivity in detecting air quality, shown in FIG. 6. It should be noted that the design of the lens needs to suit the emission spectrum of the proximity sensor 610 so that the light can be refocused to a single point. In another embodiment, to maximize a proximity detection distance, the proximity sensor 610 can provide a peak current handling of 400 mA as the supply current of the light source of the proximity sensor 610. In addition, a duty cycle of the light source of the proximity sensor 610 can be made low, enabling most light sources to handle the peak current while keeping the light source's average current. Another consideration when choosing the light source of the proximity sensor 610 is the light source's half-angle. The light source with a narrow half-angle focuses the available infrared light using a narrower beam. When the concentrated infrared light encounters an object, the reflection is much brighter. For better focusing the available infrared light to increase sensitivity, in one embodiment, the maximum detection distance of the proximity sensor 610 is set to be 3 centimeters so that light from the light source of the proximity sensor 610 is not utilized on detecting particulate matter farther away from the proximity sensor 610.

Figure 7:
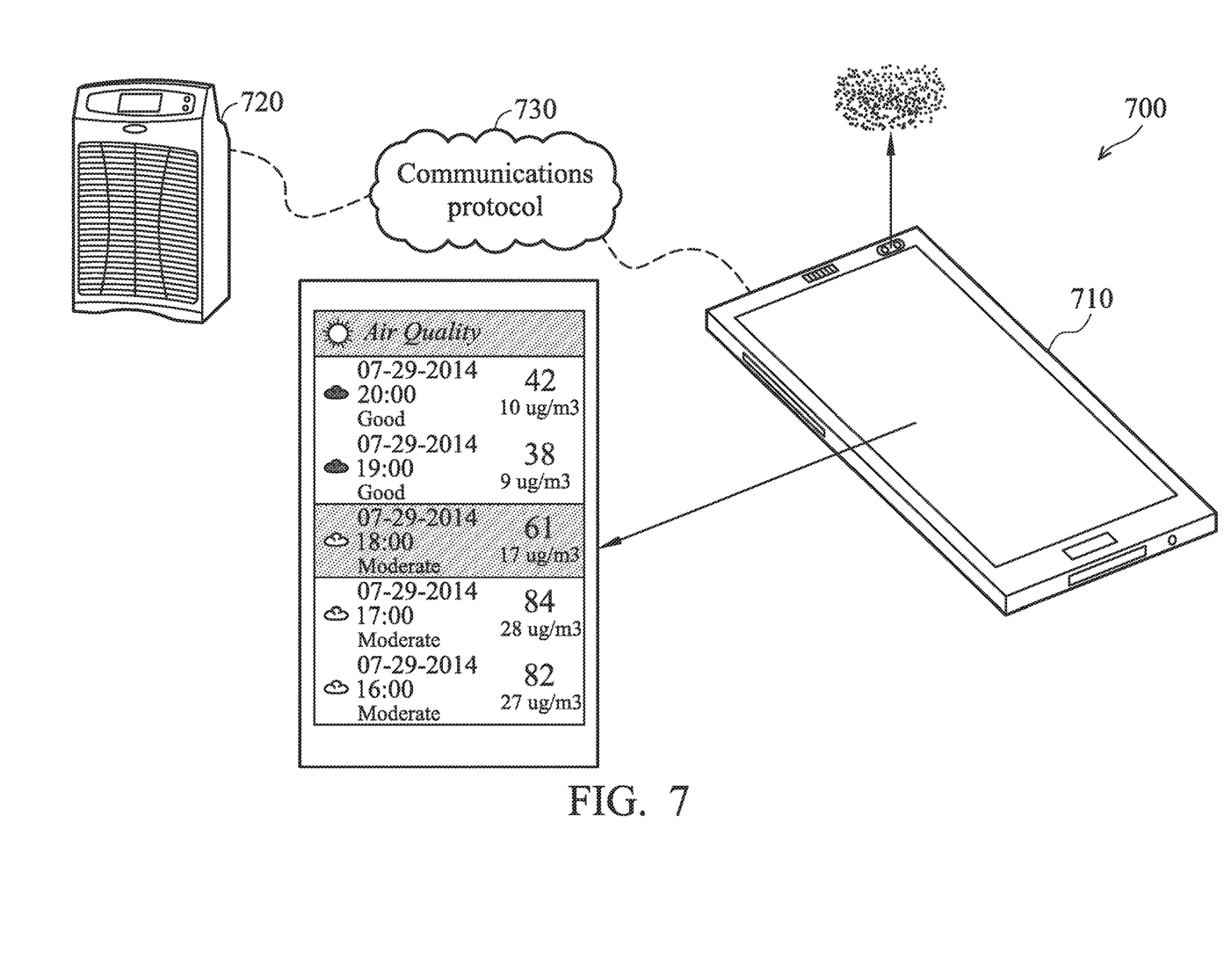
FIG. 7 illustrates a system 700 that continuously senses air quality and controls a regulator device to purify the air according to an embodiment of the present invention.

FIG. 7 illustrates a system 700 that continuously senses air quality and controls a regulator device to purify the air according to an embodiment of the present invention. The system 700 can include an electronic device 710 for sensing air quality and a regulator device 720. As shown in FIG. 7, the electronic device 710 can be utilized for realizing the electronic device 200 in FIG. 2 or the electronic device 400 in FIG. 4.

The regulator device 720 can communicate with the electronic device 710 wirelessly by using a communications protocol 730, such as Bluetooth, Wi-Fi, 3G, LTE, Wi-MAX, or any other communications protocol used by wireless devices. In one embodiment, the regulator device 720 can be a cleaning device used for purifying the air, such as, but not limited to, an air purifier.

Figure 8:
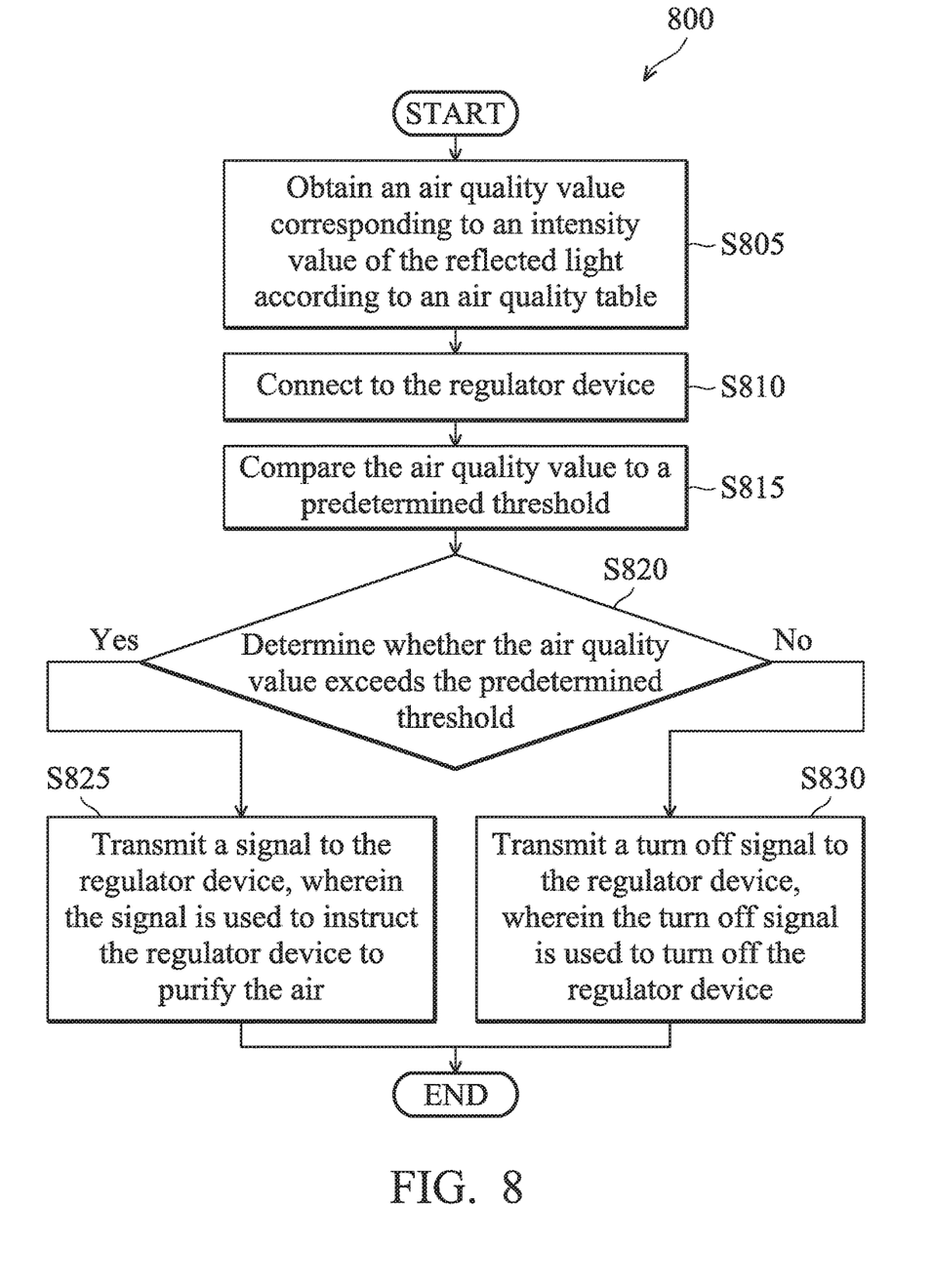
FIG. 8 is a flow diagram illustrating a method for sensing air quality according to an embodiment of the present invention with reference to FIG. 7.

FIG. 8 is a flow diagram illustrating a method 800 for sensing air quality according to an embodiment of the present invention with reference to FIG. 7. In step S805, the processor of the electronic device obtains an air quality value corresponding to an intensity value of the reflected light according to an air quality table. Basically, this step is the same as the obtaining steps in FIG. 3 and FIG. 5.

Next, in step S810, the processor connects to the regulator device. In step S815, the processor compares the air quality value to a predetermined threshold. The predetermined threshold value may be stored at various locations including, but not limited to, the memory included in the electronic device, or a cloud server communicating with the electronic device wirelessly.

In step S820, the processor determines whether the air quality value exceeds the predetermined threshold. When the processor determines that the air quality value exceeds the predetermined threshold ("Yes" in step S820), in step S825, the processor can transmits a signal to the regulator device, wherein the signal is used to instruct the regulator device to purify the air.

Referring back to step S820, when the processor determines that the air quality value does not exceed the predetermined threshold ("No" in step S820), in step S830, the processor can transmits a turn off signal to the regulator device, wherein the turn off signal is used to turn off the regulator device.

In another embodiment, the processor can also transmit another signal used to instruct the regulator device to increase/decrease the power efficiency of the regulator device, or transmit a turn on/off signal to turn on/off the regulator device.

In addition, the processor can execute the program code 214 to perform all of the above-described actions and steps or others described herein.

According to the foregoing recitations of the embodiments of the invention, it can be seen that the method and the electronic device are capable of sensing air quality by using the proximity sensor (e.g., a light-based proximity sensor). In addition, the electronic device is low cost because no hardware changes are needed for a typical electronic device that already includes a processor and a proximity sensor.

Various aspects of the disclosure have been described above. It should be apparent that the teachings herein may be embodied in a wide variety of forms and that any specific structure, function, or both being disclosed herein is merely representative. Based on the teachings herein one skilled in the art should appreciate that an aspect disclosed herein may be implemented independently of any other aspects and that two or more of these aspects may be combined in various ways. For example, an apparatus may be implemented or a method may be practiced using any number of the aspects set forth herein. In addition, such an apparatus may be implemented or such a method may be practiced using another structure, functionality, or structure and functionality in addition to or other than one or more of the aspects set forth herein. As an example of some of the above concepts, in some aspects concurrent channels may be established based on pulse repetition frequencies. In some aspects concurrent channels may be established based on pulse position or offsets. In some aspects concurrent channels may be established based on time hopping sequences. In some aspects concurrent channels may be established based on pulse repetition frequencies, pulse positions or offsets, and time hopping sequences.

Those with skill in the art will understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those with skill in the art will further appreciate that the various illustrative logical blocks, modules, processors, means, circuits, and algorithm steps described in connection with the aspects disclosed herein may be implemented as electronic hardware (e.g., a digital implementation, an analog implementation, or a combination of the two, which may be designed using source coding or some other technique), various forms of program or design code incorporating instructions (which may be referred to herein, for convenience, as "software" or a "software module"), or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

In addition, the various illustrative logical blocks, modules, and circuits described in connection with the aspects disclosed herein may be implemented within or performed by an integrated circuit ("IC"), an access terminal, or an access point. The IC may comprise a general purpose processor, a digital signal processor (DSP), an application specific integrated circuit (ASIC), a field programmable gate array (FPGA) or another programmable logic device, discrete gate or transistor logic, discrete hardware components, electrical components, optical components, mechanical components, or any combination thereof designed to perform the functions described herein, and may execute codes or instructions that reside within the IC, outside of the IC, or both. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

It should be understood that any specific order or hierarchy of steps in any disclosed process is an example of a sample approach. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented.

The steps of a method or algorithm described in connection with the aspects disclosed herein may be embodied directly in hardware, in a software module executed by a processor, or in a combination of the two. A software module (e.g., including executable instructions and related data) and other data may reside in a data memory such as RAM memory, flash memory, ROM memory, EPROM memory, EEPROM memory, registers, a hard disk, a removable disk, a CD-ROM, or any other form of computer-readable storage medium known in the art. A sample storage medium may be coupled to a machine such as, for example, a computer/processor (which may be referred to herein, for convenience, as a "processor") such that the processor can read information (e.g., code) from and write information to the storage medium. A sample storage medium may be integral to the processor. The processor and the storage medium may reside in an ASIC. The ASIC may reside in user equipment. In the alternative, the processor and the storage medium may reside as discrete components in user equipment. Moreover, in some aspects any suitable computer-program product may comprise a computer-readable medium comprising codes relating to one or more of the aspects of the disclosure. In some aspects a computer program product may comprise packaging materials.

While the invention has been described by way of example and in terms of the preferred embodiments, it is to be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An electronic device for sensing air quality, comprising:
    a proximity sensor, at least comprising:
    a light source, emitting light toward particulate matter in air, wherein the light is reflected by a surface of the particulate matter to form reflected light; and
    a light sensor, sensing the reflected light;
    a PM 2.5 filter, comprising a chamber having at least a size selective inlet, wherein the size selective inlet controls a size of the particulate matter flowing through the chamber, wherein an aerodynamic diameter of the particulate matter is less than 2.5 µm;
    a processor coupled to the proximity sensor; and
    a memory operatively coupled to the processor;
    wherein the processor is configured to execute program code stored in the memory by:
    obtaining an air quality value corresponding to an intensity value of the reflected light according to an air quality table.

2. The electronic device for sensing air quality as claimed in claim 1, wherein the air quality table is used for mapping the intensity values of the reflected light to air quality values; and the processor obtains the air quality value based on the intensity value of the reflected light.

3. The electronic device for sensing air quality as claimed in claim 1, before obtaining the air quality value corresponding to the intensity value of the reflected light according to the air quality table, the processor further executes the program code stored in the memory by:
    determining whether the PM 2.5 filter is installed at the top of the proximity sensor for controlling the size of the particulate matter flowing through the chamber; and
    obtaining a PM 2.5 quality value corresponding to the intensity value of the reflected light according to a PM 2.5 quality table after the processor determines that the PM 2.5 filter is installed at the top of the proximity sensor for controlling the size of the particulate matter flowing through the chamber.

4. The electronic device for sensing air quality as claimed in claim 3, wherein the PM 2.5 quality table is used for mapping the intensity values of the reflected light to PM 2.5 quality values; and the processor obtains the PM 2.5 quality value based on the intensity value of the reflected light.

5. The electronic device for sensing air quality as claimed in claim 1, further comprising:
    a lens, disposed on an optical path of the light source and focusing the reflected light to increase sensitivity.

6. The electronic device as claimed in claim 1, before obtaining the air quality value corresponding to the intensity value of the reflected light according to the air quality table, the processor further executes the program code stored in the memory by:
    increasing exposure time of the light sensor until a predetermined time when the intensity value of the reflected light sensed by the light sensor is less than a light threshold value.

7. The electronic device for sensing air quality as claimed in claim 1, before obtaining the air quality value corresponding to the intensity value of the reflected light according to the air quality table, the processor further executes the program code stored in the memory by:
    increasing supply current of the light source for increasing the intensity value of the light when the intensity value of the reflected light sensed by the light sensor is less than a light threshold value.

8. The electronic device for sensing air quality as claimed in claim 1, wherein the processor further executes the program code stored in the memory by:
   connecting to a regulator device;
   comparing the air quality value to a predetermined threshold;
   determining whether the air quality value exceeds the predetermined threshold; and
   transmitting a signal to the regulator device after determining that the air quality value exceeds the predetermined threshold, wherein the signal is used to instruct the regulator device to purify the air.

9. A method for sensing air quality, used in an electronic device, comprising:
   emitting, by a light source of a proximity sensor of the electronic device, light toward particulate matter in air, wherein the light is reflected by a surface of the particulate matter to form reflected light;
   sensing, by a light sensor of the proximity sensor, the reflected light;
   obtaining, by a processor of the electronic device, an air quality value corresponding to an intensity value of the reflected light according to an air quality table; and
   controlling, by a size selective inlet of a PM 2.5 filter of the electronic device, a size of the particulate matter flowing through a chamber of the PM 2.5 filter, wherein an aerodynamic diameter of the particulate matter is less than 2.5 μm.

10. The method for sensing air quality as claimed in claim 9, wherein the air quality table is used for mapping the intensity values of the reflected light to air quality values, and the method further comprises:
   determining, by the processor, the air quality value based on the intensity value of the reflected light.

11. The method for sensing air quality as claimed in claim 9, before obtaining the air quality value corresponding to the intensity value of the reflected light according to the air quality table, the method further comprises:
   determining whether the PM 2.5 filter is installed at the top of the proximity sensor for controlling the size of the particulate matter flowing through the chamber; and
   obtaining a PM 2.5 quality value corresponding to the intensity value of the reflected light according to a PM 2.5 quality table after the processor determines that the PM 2.5 filter is installed at the top of the proximity sensor for controlling the size of the particulate matter flowing through the chamber.

12. The method for sensing air quality as claimed in claim 11, wherein the PM 2.5 quality table is used for mapping the intensity values of the reflected light to PM 2.5 quality values, and the method further comprises:
   determining, by the processor, the PM 2.5 quality value based on the intensity value of the reflected light.

13. The method for sensing air quality as claimed in claim 9, wherein the electronic device further comprises a lens disposed on an optical path of the proximity sensor, and the method further comprises:
   focusing, by the lens, the reflected light to increase sensitivity.

14. The method for sensing air quality as claimed in claim 9, before obtaining the air quality value corresponding to the intensity value of the reflected light according to the air quality table, the method further comprises:
   increasing, by the processor, exposure time of the light sensor until a predetermined time when the intensity value of the reflected light sensed by the light sensor is less than a light threshold value.

15. The method for sensing air quality as claimed in claim 9, before obtaining the air quality value corresponding to the intensity value of the reflected light according to the air quality table, the method further comprising:
   increasing, by the processor, supply current of the light source for increasing luminance of the light when the intensity value of the reflected light sensed by the light sensor is less than a light threshold value.

16. The method for sensing air quality as claimed in claim 9, the method further comprising:
   connecting to a regulator device;
   comparing the air quality value to a predetermined threshold;
   determining whether the air quality value exceeds the predetermined threshold; and
   transmitting a signal to the regulator device after determining that the air quality value exceeds the predetermined threshold, wherein the signal is used to instruct the regulator device to purify the air.

* * * * *